Figure 1:
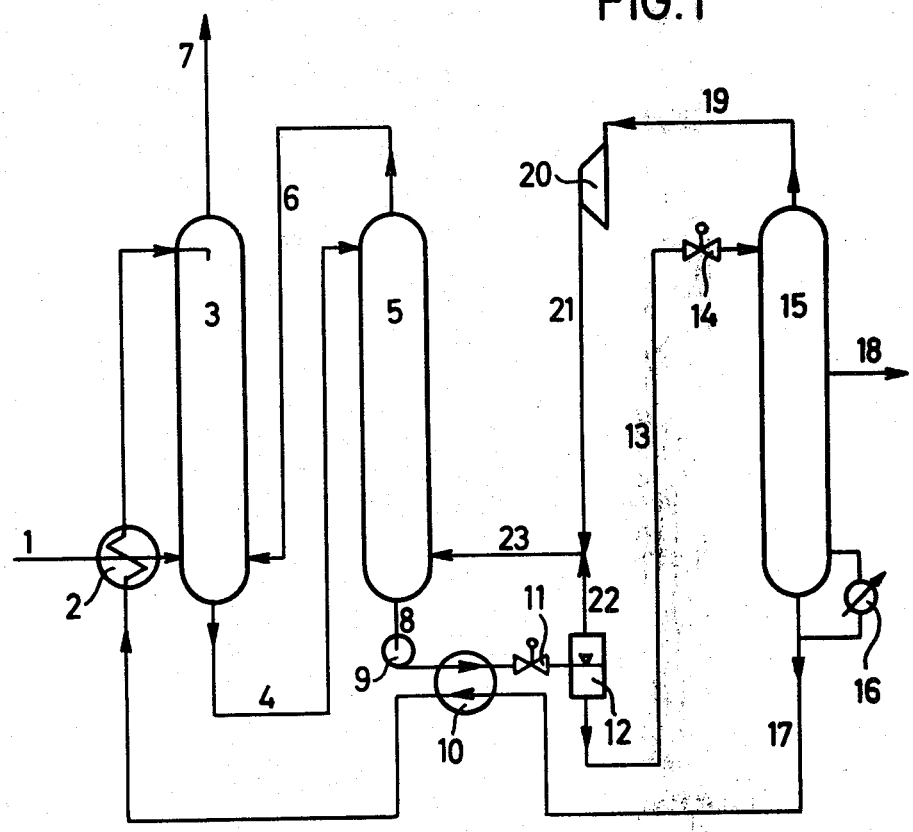

United States Patent [19]

Stockburger et al.

[11] 4,162,198
[45] Jul. 24, 1979

[54] SEPARATION OF A MIXTURE OF C₄-HYDROCARBONS BY EXTRACTIVE DISTILLATION

[75] Inventors: Dieter Stockburger, Gruenstadt; Klaus Volkamer, Frankenthal; Detlef Bender, Wachenheim; Klaus-Juergen Schneider, Neustadt; Harald Schwentker, Weisenheim; Ulrich Wagner, Limburgerhof; Hans-Martin Weitz, Bad Durkheim, all of Fed. Rep. of Germany

[73] Assignee: BASF Aktiengesellschaft, Fed. Rep. of Germany

[21] Appl. No.: 906,469

[22] Filed: May 17, 1978

[30] Foreign Application Priority Data

May 28, 1977 [DE] Fed. Rep. of Germany ....... 2724365

[51] Int. Cl.² .................. B01D 3/40; B01D 3/06; C07C 7/08
[52] U.S. Cl. ..................... 203/23; 203/78; 203/80; 203/88; 203/DIG. 19; 203/58; 585/860; 585/865
[58] Field of Search .............. 260/681.5 R, 677 A, 260/676 R; 203/23, 78, 80, 88, DIG. 19, 58, 60, 62

[56] References Cited

U.S. PATENT DOCUMENTS

| | | | |
|---|---|---|---|
| 3,436,436 | 4/1969 | Takao et al. | 260/681.5 R |
| 3,769,217 | 10/1973 | Bannister et al. | 260/681.5 R |
| 3,772,158 | 11/1973 | Sarno | 260/681.5 R |
| 3,798,132 | 3/1974 | Sarno | 260/681.5 R |
| 4,038,156 | 7/1977 | Knott et al. | 260/681.5 R |

FOREIGN PATENT DOCUMENTS

| | | | |
|---|---|---|---|
| 1519726 | 9/1976 | Fed. Rep. of Germany | 260/681.5 |
| 1158566 | 7/1969 | United Kingdom | 260/681.5 |

Primary Examiner—Wilbur L. Bascomb, Jr.
Attorney, Agent, or Firm—Keil & Witherspoon

[57] ABSTRACT

A process for separating, by means of a selective solvent, a mixture of C₄-hydrocarbons which contains some hydrocarbons which are more soluble in the selective solvent and some which are less soluble therein, in which process the hydrocarbon mixture is separated, in an extractive distillation zone, into a top product which contains the less soluble hydrocarbons and an extract which contains the more soluble hydrocarbons and the selective solvent, the extract, taken off as the bottom product, is subjected to a flash evaporation and the resulting vapor component of the extract is recycled to the extractive distillation zone while the liquid phase remaining after the flash evaporation is fed to a solvent recovery zone, in which the liquid phase obtained from the flash evaporation is separated into a product containing the hydrocarbons and, as the bottom product, the selective solvent which has been freed from the hydrocarbons, the resulting selective solvent is recycled to the extractive distillation zone and the product which is obtained from the solvent recovery zone and contains the hydrocarbons is partially or completely recycled to the extractive distillation zone, after increasing the pressure in a compression zone, in which process the extract taken off the extractive distillation zone is brought, prior to the flash evaporation to a higher pressure than the pressure in the extractive distillation zone and thereafter the extract which is under this higher pressure is heated, in a heat exchange zone, by indirect heat exchange with the selective solvent obtained as the bottom product from the solvent recovery zone, and the heated extract is subsequently let down, in the flash evaporation, to a pressure which is at least equal to the pressure in the extractive distillation zone and is higher than the pressure in the solvent recovery zone.

6 Claims, 2 Drawing Figures

SEPARATION OF A MIXTURE OF C$_4$-HYDROCARBONS BY EXTRACTIVE DISTILLATION

The present invention relates to a process for separating, by extractive distillation using a selective solvent, a mixture of C$_4$-hydrocarbons which contains hydrocarbons which are more soluble in the selective solvent and hydrocarbons which are less soluble therein.

Extractive distillation is a conventional process for separating mixtures which cannot be separated easily by conventional fractional distillation, for example if the components to be separated form an azeotrope or if the differences in their relative volatilities are small. In extractive distillation, a solvent of relatively low volatility is introduced into the distillation column in such amount that the difference in the relative volatilities of the components to be separated is increased and hence separation by distillation becomes possible. Typical examples of the use of extractive distillation are to be found, for example, in C. S. Robinson et al. "Elements of Fractional Distillation" 4th edition, McGraw-Hill Book Company, Inc., New York (1959), page 291.

German Published Application DAS 1,519,726 discloses separating a mixture of hydrocarbons of 4 carbon atoms, which contains hydrocarbons which are more soluble in a selective solvent and hydrocarbons which are less soluble therein, by an extractive distillation which is carried out in at least 2 stages under different pressure, by a method wherein the extract taken off at the bottom of the extractive distillation zone is let down, in a flash evaporation, to pressures below the pressure in the extractive distillation zone, and the vapor component formed during the flash evaporation is recycled to the extractive distillation zone.

In order to recycle the vapor phase to the extractive distillation zone, a compressor is necessary to overcome the pressure gradient. Since more than 80% of the hydrocarbons contained in the extract are evaporated during the flash evaporation, the conventional process requires a relatively large compressor with a correspondingly high consumption of electrical energy.

It is an object of the invention to provide an improved process for separating a mixture of C$_4$-hydrocarbons by extractive distillation with the aid of a selective solvent, by which process substantial savings in energy can be achieved. It is a further object of the invention to provide a process in which a smaller number of compressors, or a smaller compressor, can be used than in the conventional processes.

We have found that these objects are achieved, and other advantages obtained, according to the invention, by a process for separating, by means of a selective solvent, a mixture of C$_4$-hydrocarbons, which contains some hydrocarbons which are more soluble in the selective solvent and some which are less soluble therein, in which process the hydrocarbon mixture is separated, in an extractive distillation zone, into a top product which contains the less soluble hydrocarbons and an extract which contains the more soluble hydrocarbons and the selective solvent, the extract, taken off as the bottom product, is subjected to a flash evaporation and the resulting vapor component of the extract is recycled to the extractive distillation zone whilst the liquid phase remaining after the flash evaporation is fed to a solvent recovery zone, in which the liquid phase obtained from the flash evaporation is separated into a product containing the hydrocarbons and, as the bottom product, the selective solvent which has been freed from the hydrocarbons, the resulting selective solvent is recycled to the extractive distillation zone and the product which is obtained from the solvent recovery zone and contains the hydrocarbons is partially or, where appropriate, completely recycled to the extractive distillation zone, after increasing the pressure in a compression zone, in which process the extract taken off the extractive distillation zone is brought, prior to the flash evaporation, to a higher pressure than the pressure in the extractive distillation zone and thereafter the extract which is under this higher pressure is heated, in a heat exchange zone, by indirect heat exchange with the selective solvent obtained as the bottom product from the solvent recovery zone, and the heated extract is subsequently let down, in the flash evaporation, to a pressure which is at least equal to the pressure in the extractive distillation zone and is higher than the pressure in the solvent recovery zone.

Using the novel process, substantial savings in electrical energy are achieved. Furthermore, the number of compressors can be reduced or a substantially smaller compressor can be used than in the conventional process.

Because the extract from the extractive distillation zone has a high content of polymerizable compounds, e.g. 1,3-butadiene, vinylacetylene, ethylacetylene and 1,2-butadiene, there was a substantial prejudice against a method which entailed bringing the extract to high pressures and subsequently heating the extract, under high pressure, to a relatively high temperature in the heat exchange zone prior to flash evaporation, since under these conditions substantial deposition of polymer and contamination in the heat exchangers used in the heat exchange zone was to be expected. It was therefore surprising that no difficulties manifested themselves in the heat exchangers even after several years' running.

The process of the present application is generally applicable to the separation of mixtures of C$_4$-hydrocarbons which contain compounds of varying unsaturation. In such systems, the more saturated compound is the component which is less soluble in the selective solvent and the less saturated compound is the component which is more soluble in the selective solvent. In the case of isomers, e.g. an acetylenic compound and a diolefin, the acetylenic compound is more soluble than the diolefin.

The process of the invention is used with particular advantage for separating a mixture of C$_4$-hydrocarbons in which one constituent is 1,3-butadiene.

Such mixtures of C$_4$-hydrocarbons are obtained, for example, as C$_4$-fractions in the manufacture of ethylene and/or propylene by thermal cracking of a crude oil fraction, e.g. of liquefied petroleum gas (LPG), naphtha, gas oil or the like. Such C$_4$-fractions are also obtained on catalytic dehydrogenation of n-butane and/or n-butene. As a rule, the C$_4$-fractions contain butanes, n-butene, isobutene, 1,3-butadiene, vinylacetylene, ethylacetylene and 1,2-butadiene, with or without small amounts of hydrocarbons of 5 carbon atoms, and in general the 1,3-butadiene content is from 10 to 80 percent by weight, preferably from 20 to 70 percent by weight, and especially from 30 to 60 percent by weight, whilst the content of vinylacetylenes, ethylacetylene and 1,2-butadiene in the C$_4$-fractions in general does not exceed a total of 5 percent by weight. In the extractive distillation, according to the invention, of such a C$_4$-fraction, the saturated and monoolefinically unsaturated C$_4$-hydrocarbons, e.g. the butanes, n-butene and isobutene, are in general obtained as the top product from the extractive distillation zone, whilst 1,3-butadiene and other hydrocarbons which are more soluble in the selective solvent, e.g. vinylacetylene, ethylacetylene and 1,2-butadiene are obtained as the product of the solvent recovery zone. This butadiene obtained as the product of the solvent recovery zone is as a rule subjected to further purifications in order to obtain a very pure butadiene.

Further suitable mixtures of hydrocarbons of 4 carbon atoms, which contain 1,3-butadiene and which may be separated advantageously by the process of the invention, are crude butadienes which in general contain at least 90 percent by weight, preferably at least 95 percent by weight, and especially at least 98 percent by weight, of 1,3-butadiene and in general contain, as impurities, higher acetylenes, e.g. vinylacetylene and ethylacetylene, and higher allenes, e.g. 1,2-butadiene. Such crude butadienes are obtained, for example, by extractive distillation, e.g. by the process according to the invention, from the C$_4$-fractions obtained by thermal cracking of crude oil fractions or by catalytic dehydrogenation of n-butane and/or n-butene. When separating such a crude butadiene by the process according to the invention, 1,3-butadiene, being the hydrocarbon which is less soluble in the selective solvent, is obtained as the top product of the extractive distillation zone and the higher acetylenes and at least a part of the higher allenes, being the hydrocarbons which are more soluble in the selective solvent, are obtained as the product of the solvent recovery zone.

Examples of suitable selective solvents are carboxylic acid amides, e.g. dimethylformamide, diethylformamide, dimethylacetamide and formylmorpholine, as well as acetonitrile, furfural, N-methylpyrrolidone, butyrolactone, acetone and mixtures of these with water. The use of N-methylpyrrolidone as the selective solvent is particularly advantageous.

The extractive distillation can be carried out in a column. In the case of large tray numbers, for example with columns having more than 100 actual trays, it can be advantageous to carry out the extractive distillation in more than one column, in general in two columns. Advantageously, when using two columns, the absorption stage above the point at which the mixture of C$_4$-hydrocarbons is introduced into the extractive distillation zone will be located in the first column and the enrichment stage below the point of introduction of the hydrocarbon mixture will be located in the second column, i.e. the point at which the hydrocarbon mixture is introduced is at the top of the second column or preferably at the bottom of the first column. Preferably, a compression stage is not interposed between the absorption stage and the enrichment stage; instead, the pressure conditions maintained in the extractive distillation zone are those which result autogenously in the extractive distillation zone in the absence of compression stages and/or pressure reduction stages within the said zone, so that the pressure at the bottom of the extractive distillation zone is, in accordance with the usual pressure loss in columns, at least equal to the pressure at the top of the extractive distillation zone. As a rule, the pressure difference between top and bottom of the extractive distillation zone is from 0.1 to 3 bars, preferably from 0.2 to 2 bars.

In general, the pressure employed in the extractive distillation zone is from 1 to 9 bars, preferably from 2 to 8 bars, and especially from 3 to 7 bars. The pressure in the bottom one-third of the extractive distillation zone, i.e. in the region occupied by the lower trays of the extractive distillation zone, which correspond to about one-third of the total number of trays of the extractive distillation zone, is as a rule from 1.5 to 9 bars, preferably from 2.5 to 8 bars and especially from 3.5 to 7 bars.

The extract taken off the extractive distillation zone is first brought to a higher pressure than the pressure in the extractive distillation zone. This can be effected by, for example, a liquid pump. In general, this pressure increase takes place substantially isothermally, i.e. the only temperature changes which result are those, for example a rise of up to 1° C., which result from the steps taken to increase the pressure, for example the pumping process. In general, the extract is brought to pressures which are from 1 to 20, preferably from 2 to 18, and especially from 3 to 15, bars above the pressure in the extractive distillation zone, in particular above the pressure in the bottom one-third of the extractive distillation zone.

The extract, which is under elevated pressure, is then heated, in a heat exchange zone, by indirect heat exchange with the selective solvent obtained as the bottom product from the solvent recovery zone. After the heat exchange, the selective solvent is fed to the extractive distillation zone. As a result of the heat exchange with the selective solvent, the temperature of the extract is in general raised by from 5° to 80° C., preferably from 10° to 70° C. and especially from 15° to 60° C.

Thereafter, the heated extract is let down, by flash evaporation, to a pressure which is at least equal to the pressure in the extractive distillation zone, and preferably at least equal to the pressure in the bottom one-third of the extractive distillation zone, and is higher than the pressure in the down-stream solvent recovery zone. The essential aspect of the letting down of the pressure is that the vapor component of the extract, which forms on flash evaporation, can be recycled without a compression stage into the extractive distillation zone. Accordingly, the flash evaporation as a rule entails letting down to pressures which are from 0.05 to 2.0, preferably from 0.1 to 1, bar above the pressure at the point where the vapor component of the extract is introduced into the extractive distillation zone. The flash evaporation is carried out, for example, in a device comprising a pressure-reducing valve and an adiabatic evaporator, which may or may not be followed by a phase separation vessel for better separation of the vapor phase, formed during flash evaporation, from the liquid phase.

The combination of a heat exchange zone, for heat exchange between the extract from the extractive distillation zone and the selective solvent recycled from the solvent recovery zone, with the downstream flash evaporation can be employed in a single stage. However, it is also possible to employ more than one such combination, e.g. from 2 to 4, preferably 2 or 3, advantageously in series. By using more than one of these heat exchange/flash evaporation stages, and recycling the part-streams, thus obtained, to different feed points of the extractive distillation zone, it is possible to reduce the separating efficiency which the extractive distillation has to achieve, and to reduce the dimensions of the extractive distillation column. It is furthermore possible to interpose a further heat exchange zone between the last evaporation zone and the solvent recovery zone.

The vapor component of the extract, which forms in the flash evaporation zone or zones and which in general accounts for from 20 to 80 percent by weight, preferably from 40 to 70 percent by weight, of the hydrocarbons in the extract, is recycled to the extractive distillation zone. In general, the recycled vapor phase is introduced into the bottom one-third of the extractive distillation zone, preferably at the bottom of the said zone, for example at a point which is approximately at the height of the lowest tray of the column. In the case of a stepwise flash evaporation, the vapor components obtained from the individual stages can be recycled to the extractive distillation zone either separately or after combination with one another.

The liquid phase of the extract from the extractive distillation zone, which is left after the flash evaporation, is fed to a solvent recovery zone which is operated at a lower pressure than the pressure in the flash evaporation zone or zones. Advantageously, this residual liquid extract phase is let down to the lower pressure, prevailing in the solvent recovery zone, by means of an interposed pressure-reducing valve. In general, the pressure in the solvent recovery zone is from 0.1 to 8, preferably from 0.5 to 7, and especially from 1 to 6, bars lower than the pressure in the flash evaporation zone or zones. The solvent recovery zone can be operated as, for example, a degasser or a solvent stripper, or as a combination of these two. In general, heat is supplied to the solvent recovery zone, for example via a reboiler.

The selective solvent, freed from hydrocarbons, which is obtained as the bottom product of the solvent recovery zone is recycled to the extractive distillation zone via a heat exchange zone in which the heat exchange with the extract from the extractive distillation zone takes place.

The product obtained from the solvent recovery zone, which contains the hydrocarbons and is in general taken off as a topstream or as a topstream and a sidestream, next passes, in part or in its entirety, through a compression stage and after compression is fed to the extractive distillation zone. In the compression zone, the stream of hydrocarbon is compressed, for example in a compressor, to a pressure which is at least equal to the pressure in the extractive distillation zone. In general, the stream of hydrocarbon is compressed to pressures which are from 0.05 to 2 bars, preferably from 0.1 to 1 bar, above the pressure at the point of introduction of the vapor component of the extract into the extractive distillation zone.

As a rule, in the case of partial recycling, from 10 to 70 percent by weight, preferably from 15 to 65 percent by weight and especially from 20 to 60 percent by weight of the hydrocarbon stream obtained as the product from the solvent recovery zone are recycled to the extractive distillation zone via the compression zone. Advantageously, the compressed stream of hydrocarbon, with or without combination with the vapor component, recycled from the flash evaporation zone or zones, of the extract from the extractive distillation zone, is fed into the bottom one-third of the extractive distillation zone, advantageously at the bottom of the said zone, for example at a point near the level of the lowest column tray.

In an advantageous embodiment of the process according to the invention for isolating 1,3-butadiene from C$_4$-fractions, a crude butadiene is initally isolated, from the C$_4$-fraction, in a first extractive distillation according to the invention, this crude butadiene advantageously being taken off the solvent recovery zone, as a topstream or sidestream. Thereafter, a pure butadiene is obtained from the crude butadiene in a second extractive distillation according to the invention.

FIG. 1 schematically shows an embodiment of the process according to the invention. A mixture of C$_4$-hydrocarbons (C$_4$-fraction from an ethylene unit) is introduced, through line 1 and through evaporator 2 at the bottom of column 3, into the extractive distillation zone comprising columns 3 and 5. These two columns are connected to one another by lines 4 and 6. The selective solvent is introduced into the upper part of column 3 through line 17. A raffinate containing the saturated and monoolefinically unsaturated C$_4$-hydrocarbons is taken off at the top of column 3, through line 7. At the bottom of column 5, an extract containing the selective solvent as well as 1,3-butadiene, vinylacetylene, ethylacetylene and 1,2-butadiene is taken off through line 8. By means of the liquid pump 9, the extract taken off is brought to a higher pressure than the pressure in the extractive distillation zone and is then heated, in the heat exchanger 10, by indirect heat exchange with the selective solvent recovered as the bottom product from degasser 15. The heated extract is then passed through pressure-reducing valve 11 and let down, by flash evaporation, to a pressure which is at least equal to the pressure in the extractive distillation zone and is higher than the pressure in degasser 15. The liquid phase of the extract, obtained in phase separation vessel 12 after the flash evaporation, is passed through line 13 and through pressure-reducing valve 14 into degasser 15 and is at the same time let down to a pressure which is below the pressure in the flash evaporation zone. At the bottom of degasser 15, which is supplied with heat from reboiler 16, the selective solvent, which has been freed from the hydrocarbons in the degasser, is taken off, and is recycled through line 17, via heat exchanger 10 and evaporator 2, to the upper part of column 3.

A part of the hydrocarbons fed to the degasser via line 13 is taken off the degasser 15 as a sidestream via line 18, and can either be processed further as such or be subjected to an additional purification operation in order to obtain pure butadiene. Preferably, the crude butadiene is subjected to a second extractive distillation in accordance with the invention in order to obtain a pure butadiene.

At the top of degasser 15, the remaining part of the hydrocarbons fed, in the selective solvent, to the degasser via line 13 is taken off through line 19, compressed in compressor 20 and thereafter recycled, via lines 21 and 23, after combination with the vapor part of the extract which has formed during flash evaporation and is taken off the phase separation vessel 12 via line 22, into the lower part of column 5.

The Example which follows further illustrates the invention.

EXAMPLE

Figure 2:
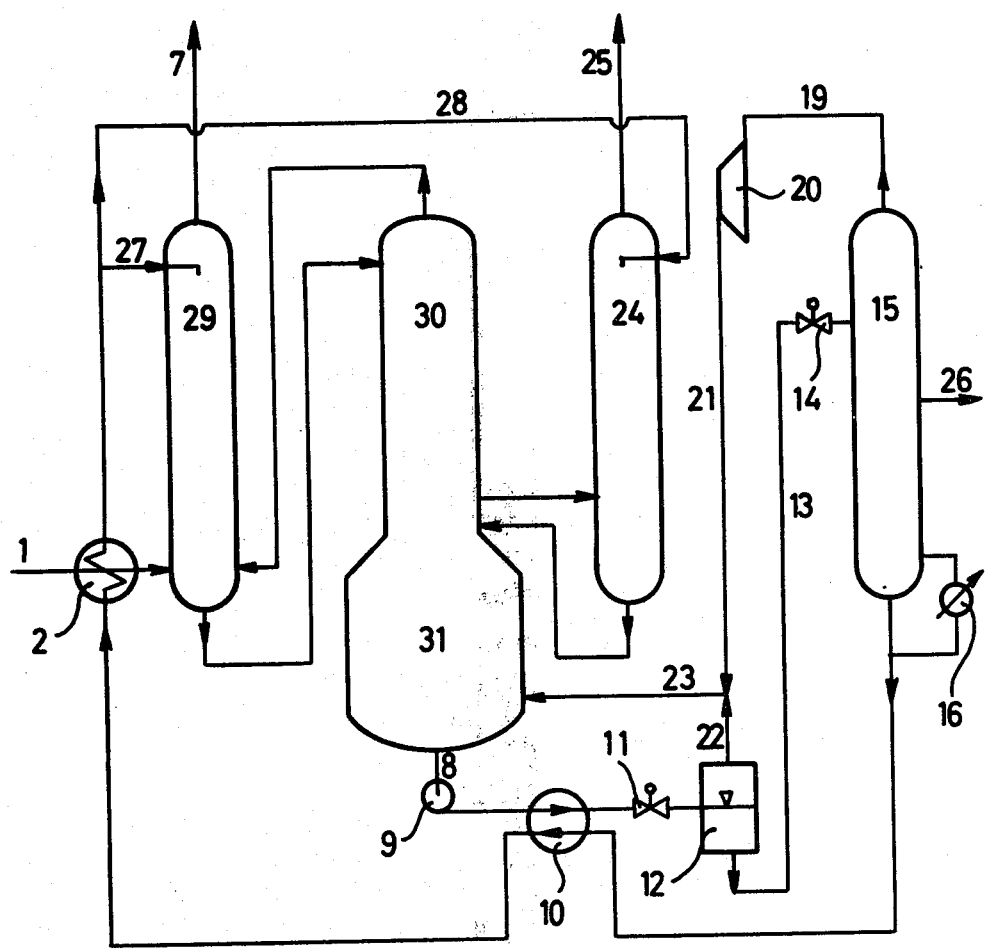

In an industrial plant for the isolation of butadiene, a mixture of C$_4$-hydrocarbons was separated in accordance with the flow chart of FIG. 2, using N-methylpyrrolidone as the selective solvent, and employing two extractive distillation zones in series. The first extractive distillation zone is formed by column 29 and the upper, narrower, column section 30, whilst the second extractive distillation zone is formed by column 24 and the lower column section 31. The selective solvent N-methylpyrrolidone is introduced into the upper part of column 21 through line 27 and into the upper part of column 24 through line 28. A mixture of hydrocarbons of 4 carbon atoms, having the composition shown in column 1 of the Table, is fed, through line 1, in an amount of 13,785.19 kg/h, into the bottom of column 21.

At the top of column 29, a raffinate of the composition shown in column 2 of the Table is taken off, in an amount of 7,381.66 kg/h, through line 7.

TABLE

|  | 1 | 2 | 3 | 4 |
|---|---|---|---|---|
| Propane | 0.03 | 0.056 | | |
| Propene | 0.10 | 0.187 | | |
| Propadiene | 0.02 | 0.037 | | |
| Propyne | 0.15 | 0.003 | 0.327 | 0.089 |
| n-Butane | 3.1 | 5.789 | | |
| i-Butane | 1.0 | 1.867 | | |
| But-1-ene | 14.0 | 26.145 | | |
| i-Butene | 26.0 | 48.557 | 0.005 | |
| trans-But-2-ene | 5.0 | 9.329 | 0.010 | |
| cis-But-2-ene | 4.3 | 7.736 | 0.350 | |
| 1,3-Butadiene | 45.0 | 0.2 | 98.801 | 26.800 |
| 1,2-Butadiene | 0.2 | — | 0.333 | 3.574 |
| 1-Butyne | 0.2 | — | 0.009 | 14.082 |
| Butanone | 0.7 | — | — | 50.276 |
| Hydrocarbons of 5 carbon atoms | 0.2 | 0.1 | 0.165 | 5.179 |

At the top of column 24, a pure butadiene of the composition shown in column 3 of the Table is obtained, in an amount of 6,211.59 kg/h, through line 25. The pure butadiene obtained can be further processed as such or be converted to a very pure butadiene by distillation.

A hydrocarbon stream, containing the acetylenes of 4 carbon atoms and having the composition shown in column 4 of the Table is taken, in an amount of 191.94 kg/h, off degasser 15 through line 26.

The pressure in the column section 31 is 5 bars. The extract taken off via line 8 is brought to a pressure of 15 bars by means of liquid pump 9 and is then heated in the heat exchanger 10 from 70° C. to 125° C. The heated extract is then passed through pressure reduction valve 11 and let down to a pressure of slightly above 5 bars. The liquid phase of the extract, contained in phase separation vessel 12 after the flash evaporation, is let down, via line 13 and through pressure reduction valve 14, to a pressure of 1.5 by releasing it into degasser 15.

At the top of the degasser, a hydrocarbon stream is taken off via line 19, compressed in compressor 20, and then recycled, via lines 21 and 23, after combination with the vapor part of the extract, taken off phase separation vessel 12 via line 22, into the lower part of column section 31.

The very small compressor has a rating of 335 kW. If, on the other hand, the butadiene is isolated in accordance with the conventional process, a substantially greater compressor, of about three times the capacity, is required, so that the electrical energy consumption of the compressor is higher by a factor of 3.

We claim:

1. A process for separating, by means of a selective solvent, a mixture of $C_4$-hydrocarbons which contains some hydrocarbons which are more soluble in the selective solvent and some which are less soluble therein and recovering the selective solvent in a solvent recovery zone, which process comprises:
   a. separating the hydrocarbon mixture, in an extractive distillation zone, into a top product which contains the less soluble hydrocarbons and an extract bottoms stream which contains the more soluble hydrocarbons and the selective solvent,
   b. passing the extract bottoms stream taken off the extractive distillation zone to a higher pressure than the pressure in the extractive distillation zone,
   c. heating the extract bottoms stream which is under this higher pressure in a heat exchange zone, by indirect heat exchange with the selective solvent obtained as the bottom product from the solvent recovery zone,
   d. subjecting the heated extract bottoms stream to a flash evaporation and letting down the pressure of the heated extract bottoms stream, in a flash evaporation, to a pressure which is at least equal to the pressure in the extractive distillation zone and is higher than the pressure in the solvent recovery zone,
   e. recycling the vapor component of the extract bottoms stream obtained from the flash evaporation to the extractive distillation zone while a liquid phase bottoms stream remaining after the flash evaporation is fed to the solvent recovery zone,
   f. separating the liquid phase bottoms stream obtained from the flash evaporation in the solvent recovery zone into a product containing the hydrocarbons and, as the bottom product, the selective solvent which has been freed from the hydrocarbons,
   g. recycling the resulting selective solvent via the heat exchange zone to the extractive distillation zone, and
   h. recycling at least a portion of the product the product which is obtained from the solvent recovery zone and contains the hydrocarbons to the extractive distillation zone, after increasing the pressure in a compression zone.

2. A process as claimed in claim 1, wherein a mixture of hydrocarbons of 4 carbon atoms which contains 1,3-butadiene is separated, the said mixture containing saturated and monoolefinically unsaturated hydrocarbons of 4 carbon atoms as the hydrocarbons which are less soluble in the selective solvent, and 1,3-butadiene, with or without higher acetylenes and 1,2-butadiene, as the hydrocarbons which are more soluble in the selective solvent.

3. A process as claimed in claim 1, wherein a crude butadiene is separated, which contains 1,3-butadiene as the hydrocarbon which is less soluble in the selective solvent and higher acetylenes, with or without 1,2-butadiene, as the hydrocarbons which are more soluble in the selective solvent.

4. A process as claimed in claim 1, wherein a mixture of hydrocarbons of 4 carbon atoms which contains 1,3-butadiene is separated, the said mixture containing saturated and monoolefinically unsaturated hydrocarbons of 4 carbon atoms as the hydrocarbons which are less soluble in the selective solvent, and 1,3-butadiene, higher acetylenes and 1,2-butadiene, as the hydrocarbons which are more soluble in the selective solvent, this separation giving a crude butadiene containing the higher acetylenes and 1,2-butadiene, which crude butadiene is subsequently separated in a second extractive distillation stage, giving very pure butadiene.

5. A process as claimed in claim 1, wherein the pressure at the bottom of the extractive distillation zone is at least equal to the pressure at the top of the extractive distillation zone.

6. A process as claimed in claim 1, wherein the combination of the heat exchange step and the downstream flash evaporation step is performed in a plurality of repeating stages.

* * * * *